(12) United States Patent
Hamilton (10) Patent No.: US 12,345,404 B2
(45) Date of Patent: Jul. 1, 2025

(54) LUMINAIRE WITH STACKED UV AND VISIBLE LIGHT SOURCES

(71) Applicant: HLI Solutions, Inc., Greenville, SC (US)

(72) Inventor: Douglas Matthew Hamilton, Arlington Heights, IL (US)

(73) Assignee: HLI SOLUTIONS, INC., Greenville, SC (US)

( * ) Notice: Subject to any disclaimer, the term of this patent is extended or adjusted under 35 U.S.C. 154(b) by 0 days.

(21) Appl. No.: 18/825,105

(22) Filed: Sep. 5, 2024

(65) Prior Publication Data

US 2024/0426473 A1     Dec. 26, 2024

Related U.S. Application Data

(63) Continuation of application No. 18/027,536, filed as application No. PCT/US2021/051073 on Sep. 20, 2021, now Pat. No. 12,111,047.

(60) Provisional application No. 63/080,876, filed on Sep. 21, 2020.

(51) Int. Cl.
| | |
|---|---|
| *A61L 2/10* | (2006.01) |
| *A61L 9/20* | (2006.01) |
| *F21V 23/04* | (2006.01) |
| *F21V 33/00* | (2006.01) |

(Continued)

(52) U.S. Cl.
CPC ............ *F21V 33/0064* (2013.01); *A61L 2/10* (2013.01); *A61L 9/20* (2013.01); *F21V 23/0442* (2013.01); *A61L 2202/11* (2013.01); *A61L 2202/14* (2013.01); *A61L 2209/111* (2013.01); *A61L 2209/12* (2013.01); *F21S 8/026* (2013.01); *F21Y 2113/10* (2016.08)

(58) Field of Classification Search
CPC .......... A61L 2/10; A61L 9/20; A61L 2202/14; A61L 2209/111; F21V 23/0442; F21V 33/0004
See application file for complete search history.

(56) References Cited

U.S. PATENT DOCUMENTS

| | | |
|---|---|---|
| 3,093,310 A | 6/1963 | Wagner |
| 4,091,441 A | 5/1978 | Ott |
| 8,113,685 B2 | 2/2012 | Wauman |
| (Continued) | | |

OTHER PUBLICATIONS

Information Disclosure Statement dated Mar. 21, 2023 which was filed in connection with U.S. Appl. No. 18/027,536.

(Continued)

*Primary Examiner* — Ismael Negron
(74) *Attorney, Agent, or Firm* — Buckley, Maschoff & Talwalkar LLC (57) ABSTRACT

A lighting system includes a housing having a light exit aperture at a distal end; a first light source configured to emit visible light; a second light source configured to emit ultraviolet light; a controller operatively coupled to the second light source; and at least one sensor operatively coupled to the controller. The second light source is disposed in the housing between the first light source and the light exit aperture, and allows at least some of the visible light emitted by the first light source to pass therethrough. In some embodiments, the controller receives one or more signals from the at least one sensor indicating detection of occupancy of the area, and in response illuminates the second light source.

18 Claims, 8 Drawing Sheets

(51) Int. Cl.
　　　*F21S 8/02*　　　　(2006.01)
　　　*F21Y 113/10*　　　(2016.01)

(56) References Cited

U.S. PATENT DOCUMENTS

| | | |
|---|---|---|
| 10,363,325 B2 | 7/2019 | Hawkins |
| 10,753,577 B2 | 8/2020 | Van Bommel |
| 11,333,347 B2 | 5/2022 | Chung |
| 11,373,854 B2 | 6/2022 | Yagyu |
| 11,628,234 B2 | 4/2023 | Basua |
| 11,833,261 B2 | 12/2023 | Chen |
| 12,111,047 B2 * | 10/2024 | Hamilton ............ F21V 23/0442 |
| 2009/0303705 A1 | 12/2009 | Waumans et al. |
| 2015/0062893 A1 | 3/2015 | Lynn et al. |
| 2018/0169279 A1 | 6/2018 | Randers-Pehrson et al. |
| 2019/0024874 A1 | 1/2019 | Van Bommel et al. |
| 2020/0179544 A1 | 6/2020 | Ufkes |
| 2022/0404012 A1 | 12/2022 | De Bevilacqua |
| 2023/0233719 A1 | 7/2023 | Kohen |

OTHER PUBLICATIONS

International Search Report and Written Opinion dated Feb. 3, 2022 which was issued in connection with PCT/US2021/051073; pp. 9.
892 Form dated Apr. 1, 2024 which was issued in connection with U.S. Appl. No. 18/027,536.

* cited by examiner

LUMINAIRE WITH STACKED UV AND VISIBLE LIGHT SOURCES

CROSS-REFERENCE TO RELATED APPLICATIONS

This application claims the benefit of co-pending U.S. application Ser. No. 18/027,536, filed on Sep. 20, 2021, which is now U.S. Pat. No. 12,222,047 and claims the benefit of U.S. Provisional Patent Application No. 63/080,876, filed Sep. 21, 2020, the entire contents of which are incorporated by reference herein.

FIELD OF THE INVENTION

Embodiments described herein relate to a luminaire having multiple light sources. Particularly, the embodiments described herein relate to a luminaire having both a visible light source and an ultraviolet light source.

SUMMARY

The present disclosure relates, in one aspect, to a luminaire. The luminaire includes a housing, a first light source, and a second light source. The housing includes a light exit aperture defined therein. The first light source is disposed in the housing. The first light source emits visible light. The second light source is also disposed in the housing. The second light source is between the first light source and the light exit aperture. The second light source emits ultraviolet light. The second light source further allows at least some of the light emitted by the first light source to pass therethrough.

The present disclosure relates, in another aspect, to a lighting system for illuminating an area. The lighting system includes a luminaire, a sensor, and a controller. The luminaire includes a first light source and a second light source. The first light source emits visible light. The second light source emits ultraviolet light. The sensor detects occupancy of the area. The controller is operatively coupled to the second light source and the sensor. The controller receives one or more signals from the sensor, determines if the area is occupied, and if the area is occupied, illuminates the second light source.

The present disclosure relates, in another aspect, to a lighting system for illuminating an area. The lighting system includes a luminaire, a light switch, and a controller. The luminaire includes a first light source and a second light source. The first light source emits visible light. The second light source emits ultraviolet light. The light switch illuminates the first light source. The controller is operatively coupled to the second light source and the light switch. The controller determines the light switch has been engaged, illuminates the second light source, and after a predetermined amount of time, turns off the second light source.

The present disclosure relates, in another aspect, to a lighting system for illuminating an area. The lighting system includes a luminaire and a controller. The luminaire includes a first light source and a second light source. The first light source emits visible light. The second light source emits ultraviolet light. The controller is operatively coupled to the second light source. The controller periodically illuminates the second light source regardless of occupancy of the area.

The present disclosure relates, in another aspect, to a method of operating a luminaire. The method includes detecting a user occupancy of an area and illuminating an ultraviolet light source, thereby emitting ultraviolet light in the area while the area is occupied by the user.

In addition, it should be understood that embodiments may include hardware, software, and electronic components or modules that, for purposes of discussion, may be illustrated and described as if the majority of the components were implemented solely in hardware. However, one of ordinary skill in the art, and based on a reading of this detailed description, would recognize that, in at least one embodiment, the electronic-based aspects may be implemented in software (e.g., stored on non-transitory computer-readable medium) executable by one or more processing units, such as a microprocessor and/or application specific integrated circuits ("ASICs"). As such, it should be noted that a plurality of hardware and software based devices, as well as a plurality of different structural components, may be utilized to implement the embodiments. For example, "servers" and "computing devices" described in the specification can include one or more processing units, one or more computer-readable medium modules, one or more input/output interfaces, and various connections (e.g., a system bus) connecting the components.

Other aspects of the embodiments will become apparent by consideration of the detailed description and accompanying drawings.

DETAILED DESCRIPTION

Figure 1:
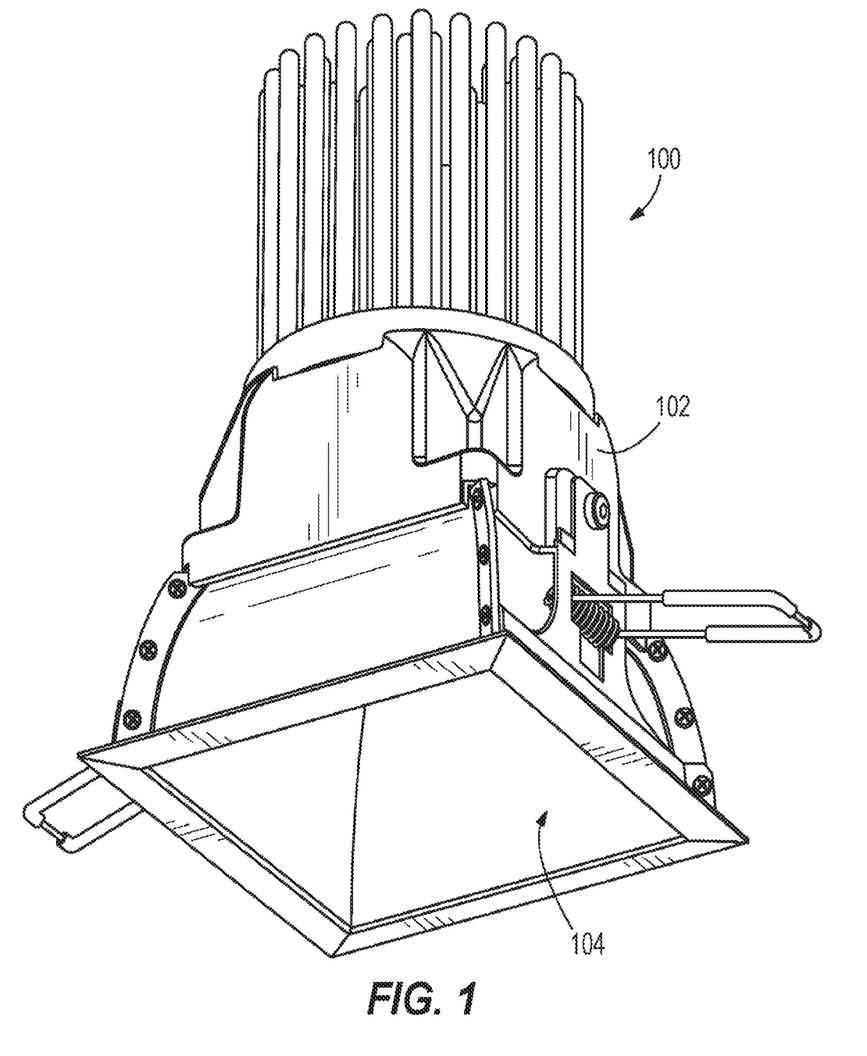
FIG. 1 illustrates a bottom perspective view of a luminaire, according to embodiments described herein.
Figure 2:
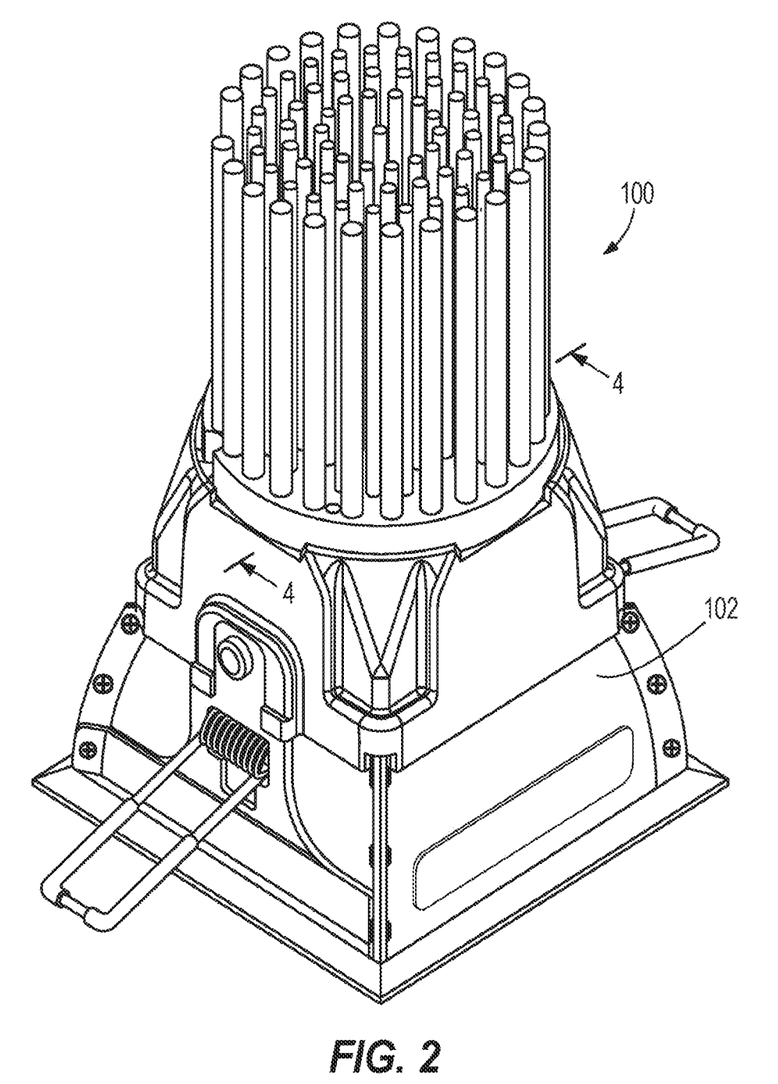
FIG. 2 illustrates a top perspective view of the luminaire of FIG. 1.

FIGS. 1 and 2 illustrate a luminaire 100. The luminaire 100 includes a housing 102. The housing 102 can be made of metal, polymer, a composite, or another material. The illustrated embodiment of the luminaire is a downlight for placement in a ceiling, but other luminaires are contemplated herein. For instance, the luminaire 100 may be an indoor luminaire or an outdoor luminaire. Further, the luminaire 100 may be for commercial or residential purposes. Example types of luminaires include, but are not limited to, linear lights, troffer lights, high-bay lights, panel lights, downlights, cylinder lights, step lights, pendant lights, track lights, flood lights, streetlamps, desk lamps, or the like.

As shown in FIG. 1, the housing 102 includes a light exit aperture 104 defined therein. The light exit aperture 104 is the opening in the housing 102 through which light exits the housing 102 and proceeds to illuminate a surrounding area, such as a room.

Figure 3:
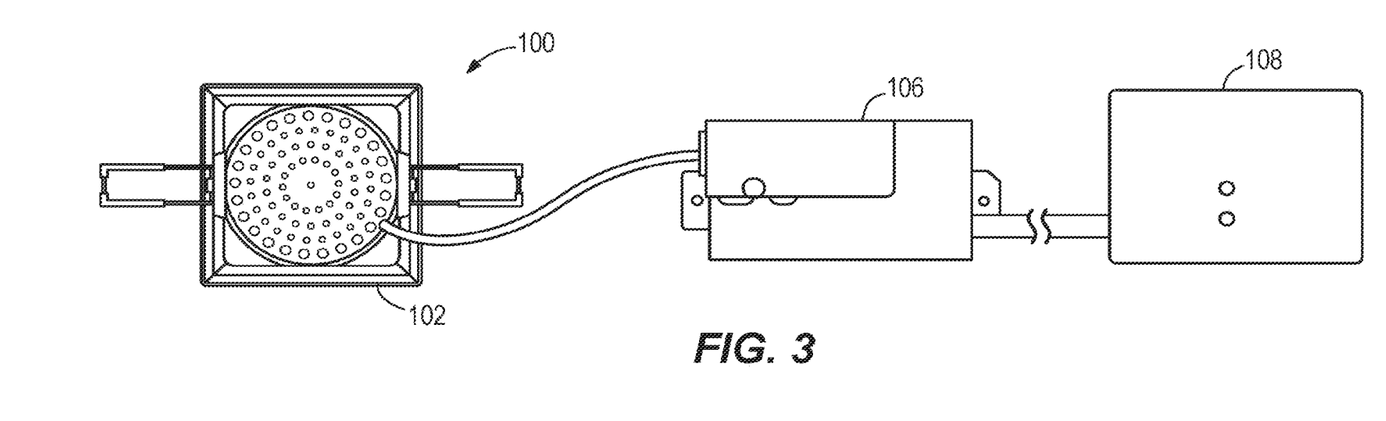
FIG. 3 illustrates a top plan view of the luminaire of FIG. 1.

Turning now to FIG. 3, a top plan view of the luminaire 100 is shown electrically coupled with a driver compartment 106 and a junction box 108. The driver compartment 106 may contain, for instance, a controller (described in more detail below). The junction box 108 may be electrically coupled with mains electricity for powering the luminaire 100 and related components. In some embodiments, however, the junction box 108 may be replaced with one or more batteries.

Figure 4:
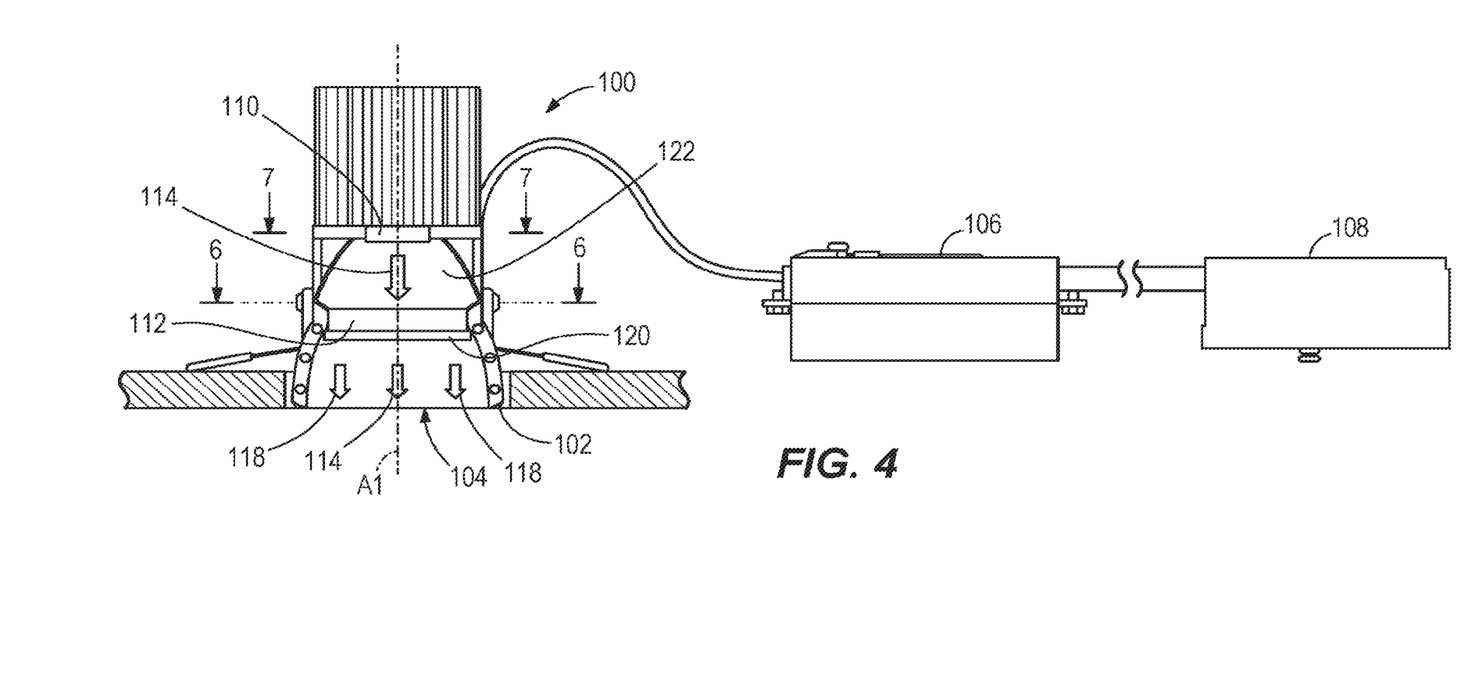
FIG. 4 is a side cross-sectional elevation view of the luminaire of FIG. 1.

With reference to FIG. 4, a cross-sectional side elevation view of the luminaire 100 is shown. The luminaire 100 further includes a first light source 110 and a second light source 112 disposed in the housing 102. The second light source 112 is disposed between the first light source 110 and the light exit aperture 104.

The first light source 110 may be, for instance, a light-emitting diode (LED) light source including one or more LEDs. Other embodiments may include other forms of the first light source 110 including, but not limited to, an incandescent light, a fluorescent light, a tungsten-halogen light, a high-intensity discharge light, an excimer light, or the like. The first light source 110 emits light 114 in the visible wavelength portion of the electromagnetic spectrum. This visible wavelength range is understood to be between 380 nanometers (nm) and 740 nm.

Figure 5:
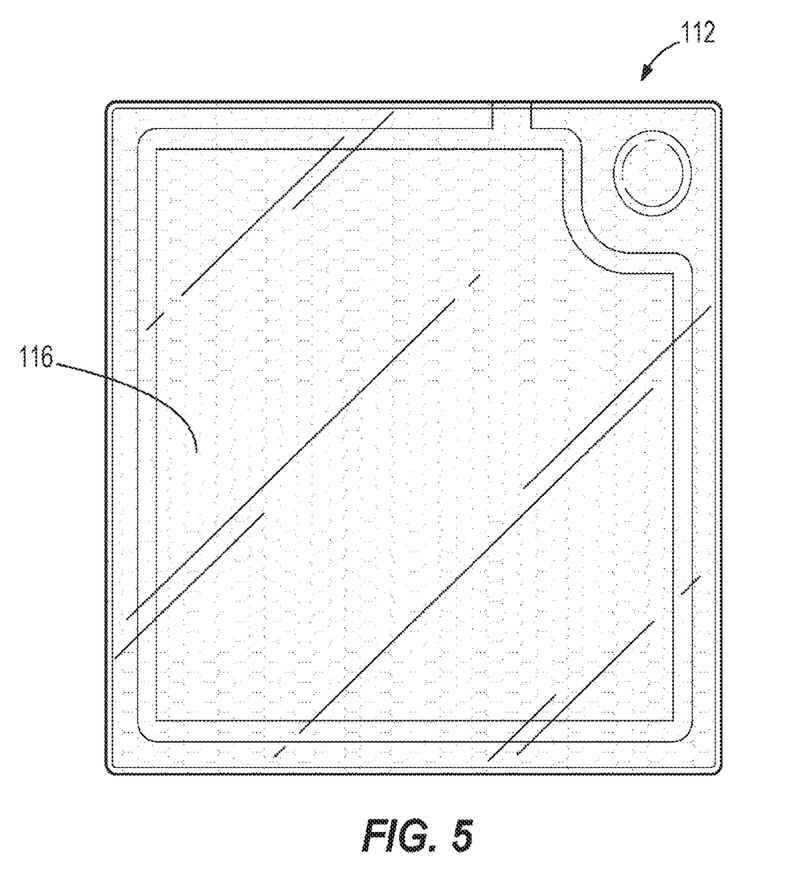
FIG. 5 illustrates an ultraviolet light source of the luminaire of FIG. 1.
Figure 6:
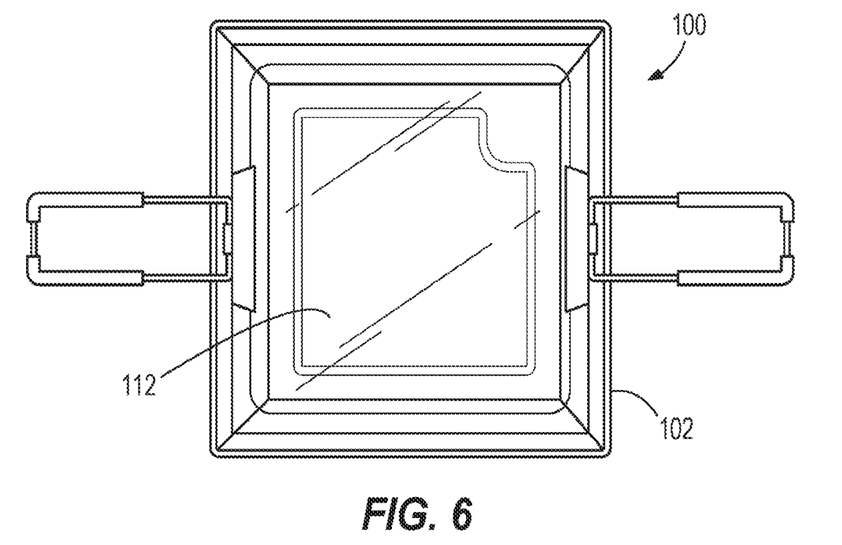
FIG. 6 illustrates a top cross-sectional plan view of the luminaire of FIG. 1.
Figure 7:
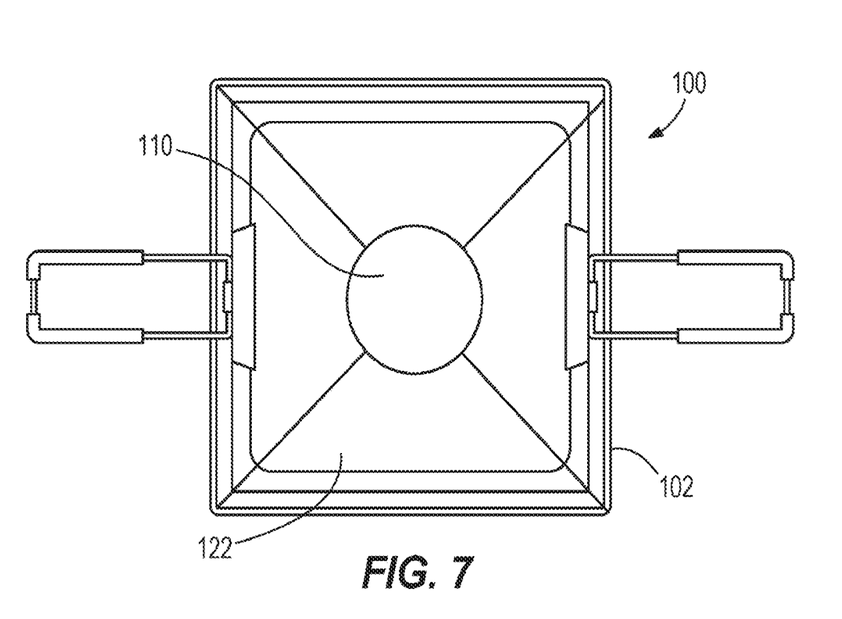
FIG. 7 illustrates another top cross-sectional plan view of the luminaire of FIG. 1.

The second light source 112 may be, for instance, an excimer light source as shown in FIG. 5. In the illustrated embodiment, the second light source 112 includes a krypton-chlorine gas disposed therein. Other embodiments of the second light source 112 are also contemplated herein as with the first light source 110. The second light source 112, in the illustrated embodiment, includes a translucent body 116. In some embodiments, at least a portion of the second light source body 114 may be transparent. This construction of the translucent and/or transparent body 116 allows at least some of the light 114 emitted from the first light source 110 to pass through the second light source 112, which will be discussed in more detail below.

Returning to FIG. 4, the second light source 112 emits light 118 in the ultraviolet (UV) wavelength portion of the electromagnetic spectrum. The UV wavelength range is understood to be between 10 nm and 400 nm. In some embodiments, the second light source 112 emits light 118 having a wavelength range that is between 200 nm and 240 nm. Some embodiments include the light 118 having a wavelength range that is between 212 nm and 232 nm. Some embodiments include the light 118 having a wavelength range that is between 217 nm and 227 nm. In the illustrated embodiment, the second light source 112 emits a majority of the light 118 with a wavelength that is 222 nm. This 222 nm wavelength is associated with what is called far-UVC light Current studies suggest that far-UVC light is safer than other wavelengths of UV light, while still being capable of killing viruses.

As mentioned briefly above, the first and second light sources 110, 112 are positioned relative to each other such that at least some of the light 114 from the first light source 110 passes through the second light source 112. Of course, although the first light source 110 has been discussed above as emitting visible light 114 and the second light source 112 has been discussed above as emitting UV light 118, these light sources could be swapped with each other. In the illustrated embodiment, the luminaire 100 further includes a central axis A1 extending therethrough. The first light source 110 and the second light source 112 are generally aligned with each other in a stacked configuration along the central axis A1 with a majority of one of the light sources 110, 112 overlapping with the other. Further in the illustrated embodiment, the central axis A1 passes through a center of each of the first and second light sources 110, 112. As such, a majority of the light 114 emitted from the first light source 110 passes through the second light source 112. The central axis A1 also passes through the center of the light exit aperture 104 in the illustrated embodiment, although other embodiments may reflect or otherwise direct the light 114, 118 away from the central axis A1 and out through the light exit aperture 104 if the light exit aperture 104 is not aligned with the light sources 110, 112.

In the illustrated embodiment, the luminaire 100 further includes a cover lens 120. In some embodiments, the cover lens 120 is a flat or planar structure. In other embodiments, the cover lens 120 may be curved or some other shape. The cover lens 120 can be made of an optically transmissive material such as, for example, clear acrylic, silicone, glass, some combination thereof, or some other material. The cover lens 120 can function to smooth edge transitions and deliver a more uniform beam of the light 114, 118. Other embodiments may be without a cover lens 120, or the cover lens 120 may alternatively be located between the first and second light sources 110, 112 instead of between the second light source 112 and the light exit aperture 104 as illustrated in FIG. 4. Of course, other embodiments may additionally or alternatively include optical films, reflectors, refractors, and/or other optical components. For instance, a reflector passage 122 is illustrated as being disposed between the first light source 110 and the second light source 112 in order to direct the light 114 away from the first light source 110 and through the second light source 112.

Figure 8:
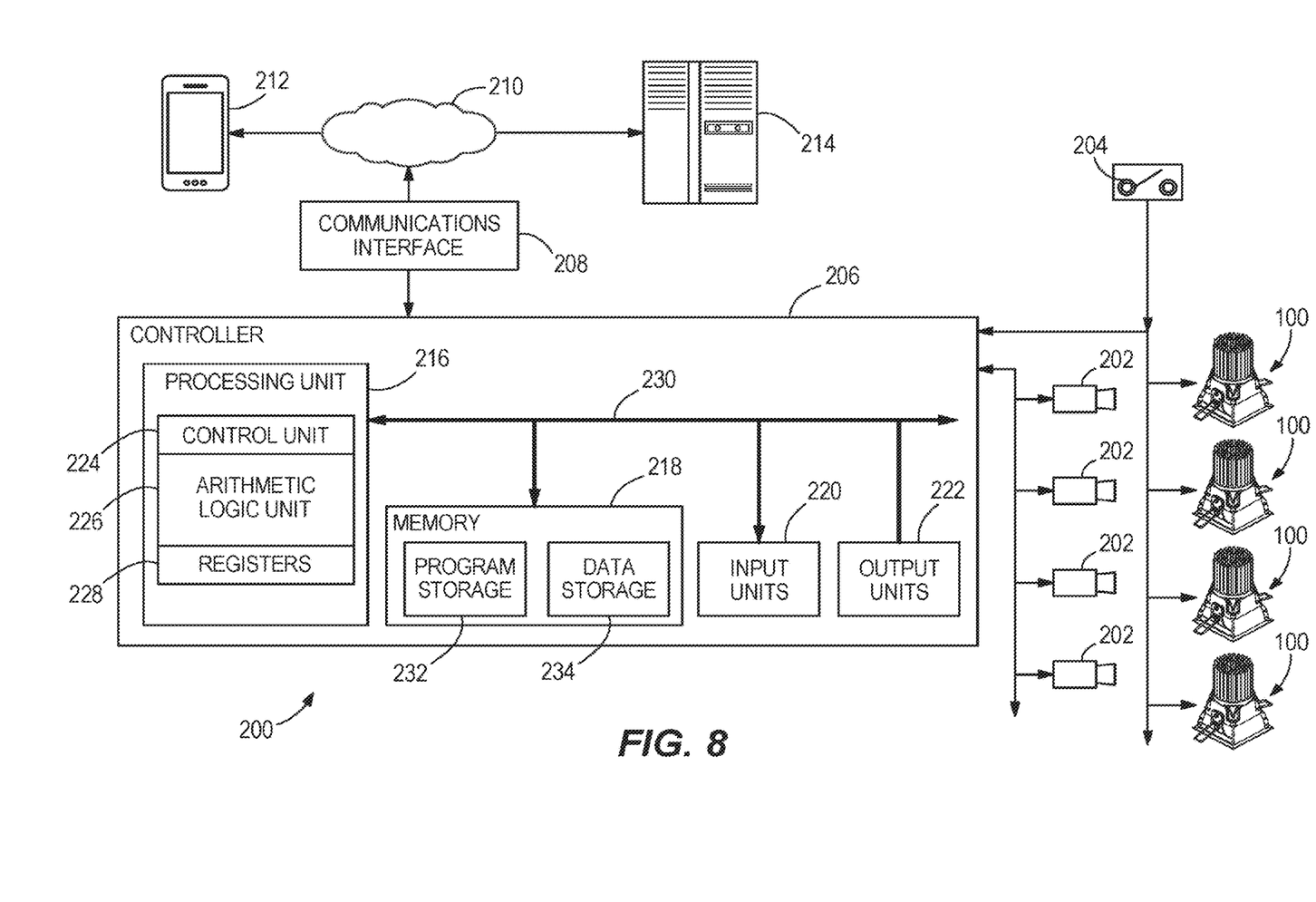
FIG. 8 schematically illustrates a system including a luminaire, according to embodiments described herein.

FIG. 8 schematically illustrates a lighting system 200 for illuminating an area, such as a room, parking garage, outdoor space, or the like. The illustrated embodiment of the lighting system 200 includes a plurality of the luminaires 100 discussed above, although other forms of luminaires may be additionally or alternatively included.

In addition to the components of the luminaire 100 discussed above, the illustrated embodiment of the lighting system 200 further includes one or more sensors 202, a switch 204 to be engaged by a user, a controller 206, a communications interface 208, a network 210, a user device 212, and a server-side mainframe computer or server 214. The user device 212 may be any appropriate device such as a personal or desktop computer, a laptop computer, a tablet computer, or a mobile phone (e.g., a smart phone).

The system 200 is provided as an example and, in some embodiments, the system 200 includes additional or fewer components. In some embodiments, the system 200 may omit the communications interface 208, the network 210, the user device 212, and the server 214. In other embodiments, the system 200 may include more than one user device 212, server 214, communication network 210, or the like.

The sensors 202 may be disposed on or in the respective luminaires 100, or the sensors 202 may be disposed remote from the luminaires 100. The sensors 202 may be any appropriate sensors for detecting occupancy including, but not limited to, motion sensors (for example, LiDAR sensors, ultrasonic sensors, or the like), thermal sensors, cameras for use with image recognition software, a user device 212 detection sensor, an audio sensor, some combination thereof, or the like.

In some embodiments, the user device 212 is configured to communicatively connect to the server 214 through the network 210 and provide information to, or receive information from, the server 214 related to the control or operation of the system 200. The user device 212 is also configured to communicatively connect to the luminaires 100 and the sensors 202 (to provide information to, or receive information from, the luminaires 100 and sensors 202). The connections between the user device 212 and the luminaires 100 and sensors 202 are, for example, wired connections, wireless connections, or a combination of wireless and wired connections. Similarly, the connections between the server 214 and the network 210 are wired connections, wireless connections, or a combination of wireless and wired connections.

The network 210 is, for example, a wide area network ("WAN") (e.g., a TCP/IP based network), a local area network ("LAN"), a neighborhood area network ("NAN"), a home area network ("HAN"), or personal area network ("PAN") employing any of a variety of communications protocols, such as Wi-Fi, Bluetooth, ZigBee, etc. In some implementations, the network 210 is a cellular network, such as, for example, a Global System for Mobile Communications ("GSM") network, a General Packet Radio Service ("GPRS") network, a Code Division Multiple Access ("CDMA") network, an Evolution-Data Optimized ("EV-DO") network, an Enhanced Data Rates for GSM Evolution ("EDGE") network, a 3GSM network, a 4GSM network, a 4G LTE network, a 5G New Radio, a Digital Enhanced Cordless Telecommunications ("DECT") network, a Digital AMPS ("IS-136/TDMA") network, or an Integrated Digital Enhanced Network ("iDEN") network, etc.

In other embodiments omitting the communications interface 208, the network 210, the user device 212, and the server 214, the controller 206 is configured to communicatively connect to the luminaires 100 and the sensors 202 (to provide information to, or receive information from, the luminaires 100 and sensors 202). The connections between the controller 206 and the luminaires 100 and sensors 202 are, for example, wired connections, wireless connections, or a combination of wireless and wired connections.

The switch 204 may be communicatively connected to the controller 206 by wired connections, wireless connections, or a combination of wireless and wired connections. Other embodiments, however, include the switch 204 coupled directly to the one or more luminaires 100 via a typical wired connection to act as a conventional light switch for the first light source 110.

The controller 206 is electrically and/or communicatively connected to a variety of modules or components of the system 200. The controller 206 includes combinations of hardware and software that are operable to, among other things, control the operation of the system 200, control the operation of the luminaires 100, control the operation of the sensors 202, receive one or more signals from the sensors 202, and, in some embodiments, communicate over the network 210, receive input from a user via the user device 212, provide information to a user via the user device 212, etc.

In the illustrated embodiment shown in FIGS. 3 and 4, the controller 206 would be associated with at least one of the luminaires 100, although other embodiments may include the controller 206 associated with the user device 212, for instance. In some embodiments, the controller 206 can provide control signals directly to the luminaires 100 and the sensors 202. In other embodiments, the controller 206 is associated with the server 214 and communicates through the network 210 to provide control signals to the luminaires 100 and the sensors 202. In the embodiments including the controller 206 associated with at least one of the luminaires 100, each luminaire 100 may be outfitted with its own respective controller 206, or a single luminaire 100 may include the only controller 206. In any instance, an example location for the controller 206 with respect to a luminaire 100 is to place the controller 206 in the driver compartment 106 illustrated in FIGS. 3 and 4.

The controller 206 includes a plurality of electrical and electronic components that provide power, operational control, and protection to the components and modules within the controller 206 and/or the system 200. For example, the controller 206 includes, among other things, a processing unit 216 (e.g., a microprocessor, a microcontroller, or another suitable programmable device), a memory 218, input units 220, and output units 222. The processing unit 216 includes, among other things, a control unit 224, an arithmetic logic unit ("ALU") 226, and a plurality of registers 228 (shown as a group of registers 228 in FIG. 8), and is implemented using a known computer architecture (e.g., a modified Harvard architecture, a von Neumann architecture, etc.). The processing unit 216, the memory 218, the input units 220, and the output units 222, as well as the various modules or circuits connected to the controller 206 are connected by one or more control and/or data buses 230 (e.g., common bus). The control and/or data buses 230 are shown generally in FIG. 8 for illustrative purposes. The use of one or more control and/or data buses 230 for the interconnection between and communication among the various modules, circuits, and components would be known to a person skilled in the art in view of the disclosure described herein.

The memory 218 is a non-transitory computer readable medium and includes, for example, a program storage area 232 and a data storage area 234. The program storage area 232 and the data storage area 234 can include combinations of different types of memory, such as a ROM, a RAM (e.g., DRAM, SDRAM, etc.), EEPROM, flash memory, a hard disk, an SD card, or other suitable magnetic, optical, physical, or electronic memory devices. The processing unit 216 is connected to the memory 218 and executes software instructions that are capable of being stored in a RAM of the memory 218 (e.g., during execution), a ROM of the memory 218 (e.g., on a generally permanent basis), or another non-transitory computer readable medium such as another memory or a disc. Software included in the implementation of the system 200 and controller 206 can be stored in the memory 218 of the controller 206. The software includes, for example, firmware, one or more applications, program data, filters, rules, one or more program modules, and other executable instructions. The controller 206 is configured to retrieve from the memory 218 and execute, among other things, instructions related to the control processes and methods described herein. In other embodiments, the controller 206 includes additional, fewer, or different components.

The direct drive signals that are provided to the luminaires 100 and/or the sensors 202 are provided, for example, based on a user input received by the controller 206 from the user device 212. The controller 206 is also configured to receive one or more signals from the sensors 202 related to scan data.

Figure 9:
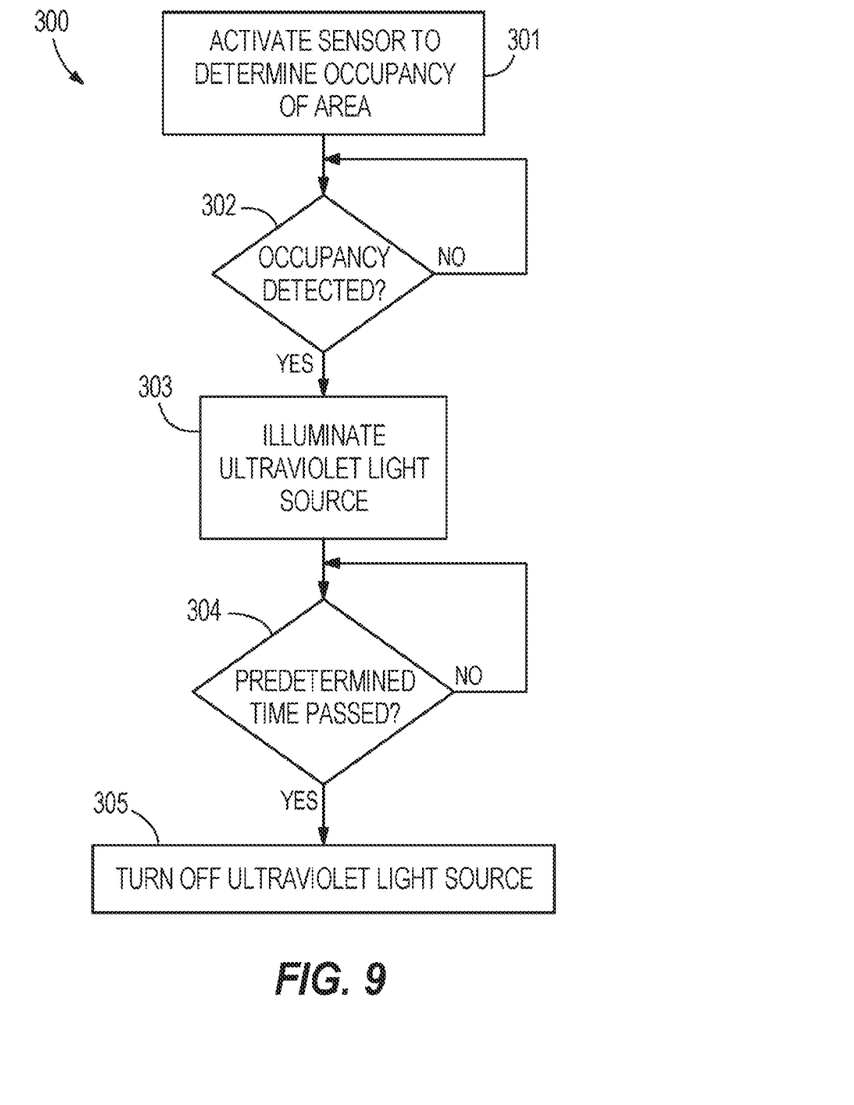
FIG. 9 illustrates a method of operating a luminaire, according to embodiments described herein.

Embodiments described herein also relate to a method 300 of operating a luminaire 100. Particularly, the flowchart illustrated in FIG. 9 is an embodiment of the method 300 utilizing the system 200 described above. The method 300 includes activating one or more of the sensors 202 to determine if the area is currently occupied (at block 301). As described above, the sensors 202 detect the presence of, for instance, a person via one or more different motion sensors (for example, LiDAR sensors, ultrasonic sensors, or the like), thermal sensors, cameras for use with recognition software, a user device 212 detection sensor, an audio sensor, some combination thereof, or the like. The controller inquires whether a signal (or lack thereof) is received from the one or more sensors 202 that corresponds to a detection of occupancy (at block 302). If no occupancy of the area is detected, the method 300 may include repeating the inquiry periodically or continuously (depending on the embodiment). If occupancy is detected and determined, the second light source 112 is illuminated by the controller 206 in order to project the UV light 118 in the area (at block 303). In the illustrated embodiment, the controller 206 times the duration of the illumination of the second light source 112 and inquires whether the time of illumination has exceeded a predetermined threshold time (at block 304). If the answer to this inquiry is no, the controller 206 continues to monitor the time while keeping the second light source 112 illuminated. If the answer to the inquiry is yes, the controller 206 proceeds with turning off the second light source 112 (at block 305).

Of course, the above described method 300 is just one example of how the system 200 may operate. The method 300 is silent as to the operation of the first light source 110. In some embodiments, the user may operate the first light source 110 directly with a conventional light switch 204. In other embodiments, the first light source 110 may also be activated by the controller 202 in response to a detection of occupancy in the area.

It is important to note, however, that the purpose of the first light source 110 is different from the purpose of the second light source 112. Particularly, the first light source 110 operates to illuminate the room with visible light 114 as is the case with typical lights. The second light source 112 operates to kill viruses and/or bacteria on surfaces and/or in the air. As such, the second light source 112 usually does not need to be illuminated for the same length of time as the first light source 110.

For instance, some studies have shown approximately 25 minutes of illumination of the area with the far-UVC light 118 kills about 99.9% of airborne viruses. As such, the timer may, for instance, cause the controller 206 to turn off the second light source 112 after the 25 minutes have elapsed, while the first light source 110 may remain illuminated to allow a user to see and work in the area. Other embodiments may turn off the second light source 112 after more or less than 25 minutes such as, for instance, 5 minutes, 10 minutes, 15 minutes, 30 minutes, or the like.

The illustrated method 300, however, only inquires whether the area is occupied for a first time. A user may instruct the controller 206 to begin this method 300, or the method 300 may be performed periodically automatically. This method 300 may operate only once a day, for instance. Other versions of the method 300 may operate to activate the sensors periodically, such as twice a day, three times a day, once every two days, or the like. Such embodiments may further include an inquiry as to whether another predetermined amount of time has passed since the second light source 112 has been turned off. If the predetermined amount of time since the second light source 112 has been turned off has passed, the method 300 may return to block 301 to activate the sensor(s) 202 once more.

In embodiments with the controller 206 operating the first light source 110 due to input from the sensor(s) 202, the controller 206 may inquire periodically whether the area is occupied, as with traditional motion sensor lights used today. In such embodiments, the user may leave the area after a short amount of time such as, for instance, 1 minute. Such a situation may function to activate the second light source 112 per the method 300 and additionally to activate the first light source 110 as described above. In this situation, the controller 206 may recognize, for instance, 2 minutes after the user enters the room, that the user has left 1 minute ago. The controller 206 would then shut off the first light source 110. The second light source 112, in most embodiments, has not yet been illuminated for the predetermined threshold amount of time. As such, the second light source 112 would continue to project the UV light 118 until the predetermined threshold amount of time has passed. Because the UV light 118 is not in the visible spectrum, the user will not notice the second light source 112 remains illuminated and will perceive the room as being dark after the first light source 110 has been turned off.

Figure 10:
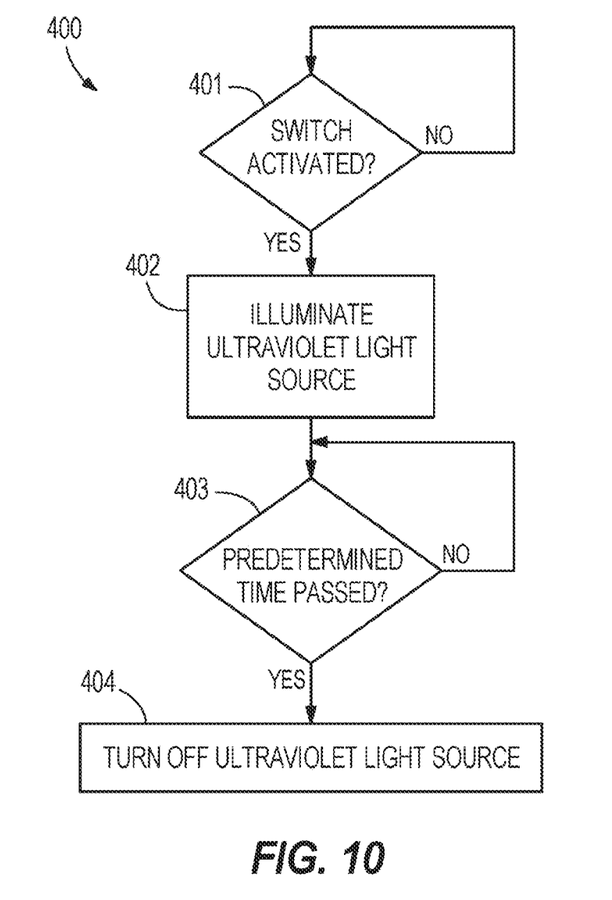
FIG. 10 illustrates another method of operating a luminaire, according to embodiments described herein.

In embodiments of the system 200 that include the light switch 204, the controller 206 may operate according to another method 400. The flowchart illustrated in FIG. 10 is an embodiment of the method 400 utilizing the system 200 described above, but without the sensors 202. Instead, the controller 206 may detect activation of the light switch 204 instead of utilizing the other sensors discussed above. The method 400 includes the controller 206 inquiring, either periodically or continuously, whether the light switch 204 has been activated (at block 401). Upon detecting the light switch 204 has been engaged, the controller 206 begins illuminating the second light source 112 (at block 402). The controller may detect the light switch 204 has been activated by monitoring, for instance, the flow of electricity through a circuit including the light switch 204. The controller 206 then inquires whether the predetermined amount of time has passed (at block 403). This inquiry may occur periodically or continuously. After the predetermined amount of time has passed, the controller 206 turns off the second light source 112 (at block 404). As discussed above, the method 400 could further include another inquiry as to whether another predetermined period of time has passed since the second light source 112 was last turned off. In such embodiments, once the predetermined period of time has passed since the second light source 112 has been turned off, the method 400 may begin again at block 401. In such embodiments, this additional time inquiry prevents the system 200 from activating the second light source 112 more often than is necessary due to users frequenting the area and/or repeatedly activating the light switch 204.

In still other embodiments, the system 200 may periodically illuminate the area with the UV light 118 from the second light source 112 regardless of occupancy of the area. This timed illumination, as well as many of the other embodiments described above, is possible in embodiments utilizing UV light 118 in a wavelength range that has been studied to be much safer for users, whereas previous UV light sources would need to operate only while a room is unoccupied.

Although certain aspects have been described in detail with reference to the above disclosed embodiments, variations and modifications exist within the scope and spirit of one or more independent aspects as described. Various features and advantages are set forth in the following claims.

What is claimed is:

1. A lighting system for illuminating an area comprising:
   at least one luminaire disposed in an area, the at least one luminaire comprising:
   a housing having a light exit aperture at a distal end, a first light source configured to emit visible light, and a second light source configured to emit ultraviolet light, wherein the second light source is disposed in the housing between the first light source and the light exit aperture and allows at least some of the visible light emitted by the first light source to pass therethrough;

a controller operatively coupled to the second light source of the at least one luminaire; and at least one sensor operatively coupled to the controller and disposed at least one of on the at least one luminaire or remote from the at least one luminaire.

2. The lighting system of claim 1, wherein the controller is configured to illuminate the first light source in response to the one or more signals.

3. The lighting system of claim 1, further comprising a switch operatively coupled to the at least one luminaire and to the controller, and wherein the controller is configured to illuminate the first light source in response to operation of the switch by a user.

4. The lighting system of claim 1, wherein the at least one sensor comprises one of a motion sensor, a temperature sensor, or an audio sensor.

5. The lighting system of claim 1, wherein the wavelength of a majority of the ultraviolet light emitted by the second light source is between 212 nanometers and 232 nanometers.

6. The lighting system of claim 1, wherein the wavelength of a majority of the ultraviolet light emitted by the second light source is between 217 nanometers and 227 nanometers.

7. The lighting system of claim 1, wherein the wavelength of a majority of the ultraviolet light emitted by the second light source is 222 nanometers.

8. The lighting system of claim 1, wherein the controller is configured to:

receive one or more signals from the at least one sensor indicating detection of occupancy of the area, and in response to receiving the one or more signals, illuminate the second light source.

9. The lighting system of claim 8, wherein the controller is configured to:

determine that illumination of the second light source has exceeded a predetermined threshold time; and turn off the second light source.

10. The lighting system of claim 1, further comprising:

a communications interface operatively coupled to the controller; and a user device operatively coupled to the communications interface via a network.

11. The lighting system of claim 10, wherein the user device at least one of provides information to or receives information from, via the communications interface, at least one of the at least one luminaire and the at least one sensor.

12. The lighting system of claim 10, further comprising a server operatively coupled to the user device and the communications interface via a network.

13. The lighting system of claim 12, wherein the server is operable to, via the network, at least one of provide information to and receive information from the user device concerning at least one of control and operation of the lighting system.

14. The lighting system of claim 1, wherein the controller is further operatively coupled to the first light source and configured to:

receive the one or more signals from the at least one sensor; and illuminate the first light source.

15. The lighting system of claim 14, wherein the controller is further configured to determine when the area is unoccupied for a threshold amount of time after illuminating the first light source and then turn off the first light source.

16. The lighting system of claim 14, further comprising a switch operatively coupled to the controller.

17. The lighting system of claim 16, wherein the controller is configured to:

determine that the light switch has been engaged;

illuminate the second light source;

determine that a predetermined amount of time has expired; and turn off the second light source.

18. The lighting system of claim 16, wherein the controller is configured to determine that the light switch has been engaged and is configured to periodically illuminate the second light source regardless of occupancy of the area.

* * * * *